(12) United States Patent
Hentrich et al.

(10) Patent No.: US 8,784,785 B2
(45) Date of Patent: Jul. 22, 2014

(54) TEMPERATURE-RESISTANT STYLING MEDIUM

(75) Inventors: Dirk Hentrich, Hamburg (DE); Winfried Emmerling, Tornesch (DE); Helga van Flodrop, Hamburg (DE)

(73) Assignee: Henkel AG & Co. KGaA, Dusseldorf, DE (US)

( * ) Notice: Subject to any disclaimer, the term of this patent is extended or adjusted under 35 U.S.C. 154(b) by 1062 days.

(21) Appl. No.: 11/569,065

(22) PCT Filed: May 17, 2005

(86) PCT No.: PCT/EP2005/005338
§ 371 (c)(1),
(2), (4) Date: Nov. 13, 2006

(87) PCT Pub. No.: WO2005/112878
PCT Pub. Date: Dec. 1, 2005

(65) Prior Publication Data
US 2008/0230084 A1    Sep. 25, 2008

(30) Foreign Application Priority Data
May 18, 2004    (WO) ................ PCT/EP2004/005317

(51) Int. Cl.
*A61Q 5/06*    (2006.01)

(52) U.S. Cl.
USPC .................................... 424/70.15; 424/70.11

(58) Field of Classification Search
None
See application file for complete search history.

(56) References Cited

U.S. PATENT DOCUMENTS

| | | | |
|---|---|---|---|
| 2,390,073 A | 12/1945 | Calva | |
| 4,374,125 A | 2/1983 | Newell | |
| 5,256,407 A * | 10/1993 | Gough | 424/70.11 |
| 5,840,329 A * | 11/1998 | Bai | 424/458 |
| 6,056,946 A * | 5/2000 | Crudele et al. | 424/70.12 |
| 6,241,977 B1 | 6/2001 | McMullen | |
| 6,475,475 B2 * | 11/2002 | Birkel et al. | 424/70.15 |
| 6,656,457 B2 * | 12/2003 | Kamis et al. | 424/70.2 |
| 2002/0182163 A1 | 12/2002 | Cannell | |

FOREIGN PATENT DOCUMENTS

| | | |
|---|---|---|
| DE | 44 13 686 C2 | 10/1995 |
| DE | 44 40 625 A1 | 5/1996 |
| DE | 195 03 465 A1 | 8/1996 |
| EP | 0 612 759 B1 | 8/1994 |
| EP | 0715842 A | 6/1996 |
| WO | WO 8904653 A | 6/1989 |

* cited by examiner

*Primary Examiner* — Jyothsna Venkat
(74) *Attorney, Agent, or Firm* — Ingrassia Fisher & Lorenz, P.C.

(57) ABSTRACT

The invention relates to cosmetic preparations for treating the hair containing exclusively ingredients which are stable up to at least 200 DEG C against thermal decomposition and the use of such preparations for shaping the hair and a method for temporary hair-shaping.

5 Claims, 8 Drawing Sheets

Onset of oxidative decomposition at 290.00 °C

Figure 3

Sample dried overnight at room temperature
20 °C/min / ca. 35 mg / 3 l/h air or $N_2$ / Al pan 1, open ———— $N_2$ Luviquat Style

- - - - - - - - air Luviquat Style

Onset of oxidative decomposition at 257.31 °C

Figure 4

Sample dried overnight at room temperature
20 °C/min / ca. 26-28 mg / 3 l/h air or N₂ / Al pan 1, open —————— N₂ Luviquat Hold HS 11896 TR

- - - - - - - - air Luviquat Hold HS 11896 TR

Onset at 227.64 °C

Figure 5

———— N₂ Styleze W-20 LMA 238 TR

-------- air Styleze W-20 LMA 238 TR

Onset of oxidative decomposition at 245.00 °C

Evaporation of residual solvent 20-170 °C

Figure 6

Sample dried overnight at room temperature
20 °C/min / 25-26 mg / 3 l/h air or $N_2$ / Al pan 1, open ——— $N_2$ PVP/VA copolymer HS 13081 TR
- - - - - - - air PVP/VA copolymer HS 13081 TR Onset at 202.47 °C

Figure 7

Onset of oxidative decomposition at 292.38 °C

Figure 8

20 °C/min / 6-7 mg / 3 l/h air or N$_2$ / Al pan 1, open

———— N$_2$ Phenylethyl alcohol

- - - - - - - - - air Phenylethyl alcohol

TEMPERATURE-RESISTANT STYLING MEDIUM

The present invention relates to cosmetic preparations for hair treatment, comprising exclusively ingredients that are stable up to at least 200° C. against thermal decomposition, and the use of such preparations for styling the hair and a method for temporary hair-styling.

Nowadays, many treatments are carried out on keratinic fibers, especially human hair. Treatments, which provide a permanent or temporary hairstyling, to maintain suitably looking hairstyles, play an important role here. Based on actual fashion trends, time and again hairstyles are considered chic, which, for many types of hair, can only be formed or sustained over a longer period by the use of certain consolidating materials. Examples of temporary hairstyles include styles like curling, straightening, teasing or also setting. Temporary styling intended to provide a good set, without compromising the healthy appearance of the hair, such as, for example the gloss, can be obtained by the use of styling media, such as hairsprays, hair waxes, hair gels, setting lotions, curlers, styling sprays etc. Temporary styling is also called hair styling or styling and the products are also called styling products.

Similarly, hair setting under the action of heat, e.g. from a hair-dryer, a curling rod or a hot iron also play an important role in the field of hair styling. To improve styling results, a styling product, e.g. a hair setter or a styling spray, is often applied to the hair and in the case of higher temperatures, also a thermal styling spray, prior to a heat treatment. In particular, hairdressers use hot irons more and more often. Hot irons have two parallel metallic or ceramic plates, through which, after they have been heated, the hair is threaded by moving the hot iron along the strand of hair. Commercial hot irons are heated to temperatures in the range 150-250° C. The hot irons are used to thermally or physically straighten permed or curly hair. When hot irons are used to straighten hair, then beforehand a thermal styling spray, also called a hot iron spray, is usually applied to the hair as the hot iron styling agent. The spray helps the iron to slip along and helps to straighten the hair.

Hair setting using the effects of heat are also employed for the opposite effect, namely to set or crimp straight hair. In this case, a curling rod or also a hair-dryer with a diffuser is used instead of a hot iron. Here, the straight hair is wrapped round the heated curling rod or the diffuser, temperatures of up to 250° C. again being reached. In this case, thermal styling sprays are also generally used to improve the styling result and are applied to the hair prior to the actual heat treatment.

For a more pleasant experience, these styling compositions also comprise inter alia perfumes, besides hair-care additives and hair-setting active substances that are generally polymeric active substances. The substances comprised in these compositions are exposed to extremes of heat, particularly with hair styling involving hot irons or curling rods that often reach temperatures of up to 250° C.

Numerous cosmetic compositions are known from the prior art for hair styling and also for use under heat treatment.

The disadvantage of the cosmetic compositions for hair-styling under heat treatment, known from the prior art, is their intensive unpleasant smell on heating, which can often cause a slight coughing stimulus during the heat treatment of the hair. It is suspected that such thermal styling sprays, i.e. setting sprays, known from the prior art and which are intended for use on hair under the action of heat at temperatures of up to 150-250° C., release one or other toxicologically non-harmless substances that the user inhales. This can lead to adverse health effects that are particularly relevant for the persons working in the hair salon, who often carry out many thermal hair settings on a daily basis, using thermal styling sprays or styling agents for hot irons.

Accordingly, the object of the present invention was to provide a safe cosmetic composition for treating hair under thermal conditions, i.e. a toxicologically harmless composition that also remains toxicologically harmless at use temperatures of up to 200° C. A further object of the invention was to provide a cosmetic composition for treating hair under thermal conditions in the range of up to 200° C., which exhibits a significantly reduced odour formation at these temperatures in comparison with conventional compositions and is therefore considerably more agreeable when used.

These objects are achieved in an outstanding manner by the provision of a cosmetic composition for treating hair, which exclusively comprises ingredients that are stable up to 200° C. towards thermal decomposition.

Accordingly, a first subject matter of the invention is a cosmetic composition for treating hair, which exclusively comprises ingredients that are stable up to 200° C. towards thermal decomposition. The dependent claims illustrate preferred embodiments of the subject matter of this invention.

A further subject matter of the invention is the use of this composition for styling hair, wherein the dependent claims illustrate preferred embodiments.

Finally, a further subject matter of the invention is a method of hairstyling. The dependent claims concern a preferred method.

The various embodiments will hereinafter be described in conjunction with the following drawing figures, wherein like numerals denote like elements, and wherein.

In the context of the investigations on which the present invention is based, it was surprisingly found that cosmetic compositions that exclusively comprise ingredients that are thermally stable up to 200° C. do not cause any unpleasant odors when used for hairstyling, e.g. as styling agents for hot irons or curling rods, and are suitable and safe to use.

The investigations demonstrated that the ingredients of the styling sprays known from the prior art are not stable under thermal conditions of up to 150-250° C., and also decompose to generate gaseous decomposition products such as e.g. glycerin. Concerning glycerin, for example, it is known that vegetable oils, when heated in a pan up to about 200° C., decompose into glycerin and fatty acids, which on further heating decomposes affording an unpleasant smell. Moreover, it is also presumed that perfumes also decompose at temperatures below 200° C. and yield an unpleasant smell.

The gaseous decomposition products reach the user through the air and can provoke a coughing stimulus as well as leading to an encroachment on the well being.

This problem of the decomposition of the ingredients of thermal styling sprays at the usual application temperatures of a treatment with a hot iron or a curling rod has not been described in the prior art. The ingredients of the thermal styling sprays known from the prior art do not differ from those of the styling sprays that are destined for hair setting at low temperatures of up to 80° C. The extreme conditions of heat when using a hot iron or a curling rod for treating hair were evidently not taken into consideration in the development of the thermal styling sprays known from the prior art, rather typical ingredients of known styling sprays were also employed, independently of their stability towards high temperatures.

The inventive compositions provide a significant increase in safety when using styling agents e.g. for the treatment using hot irons as well as a more pleasant handling.

Surprisingly, it was determined that inventive compositions moreover afford a significantly improved durability to the straightening when compared with the thermal styling sprays known from the prior art. The same is true for their use in connection with hair curling when using a curling rod.

In the investigations on which this invention is based, the decomposition temperature of the ingredients was determined by means of differential scanning calorimetry, DSC) as the first exothermic deviation of a DSC measurement in an atmosphere of air from a DSC measurement in a nitrogen atmosphere. The measurements were carried out under standard conditions in a Universal V3.8 B TA Instruments apparatus or a Universal V3.9 A TA Instruments apparatus in an aluminum pan with a heating rate of 20° C./min, a sample weight of 6-7 mg and a nitrogen or air supply of 3 l/h. The ingredients in the inventive compositions, such as e.g. protein hydrolyzates, polymers, surfactants, silicone oils or aromas, all have a decomposition temperature greater than 200° C., measured according to the above method. However, the invention is not limited to compositions that comprise ingredients that have a decomposition temperature greater than 200° C., measured according to the above method. It also includes compositions whose ingredients have a decomposition temperature of over 200° C., determined according to other methods, such as e.g. the capillary method.

Figure 1:
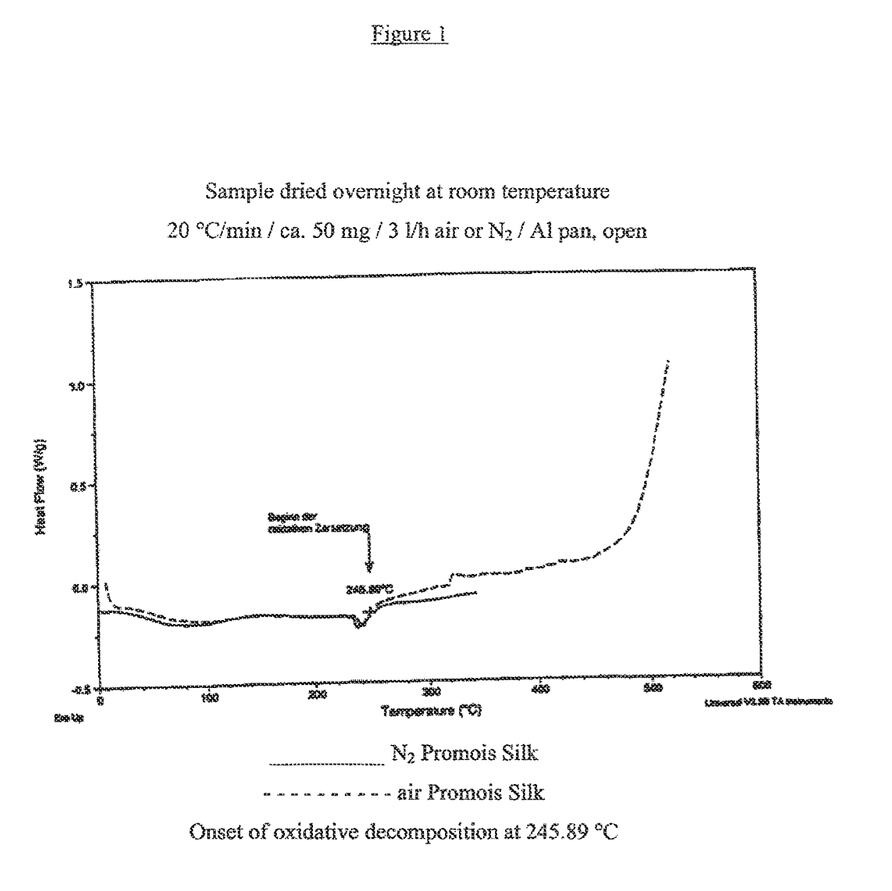
FIG. 1 is a graph showing DSC measurements under an air atmosphere and under nitrogen for Promois Silk protein hydrolyzate.
Figure 2:
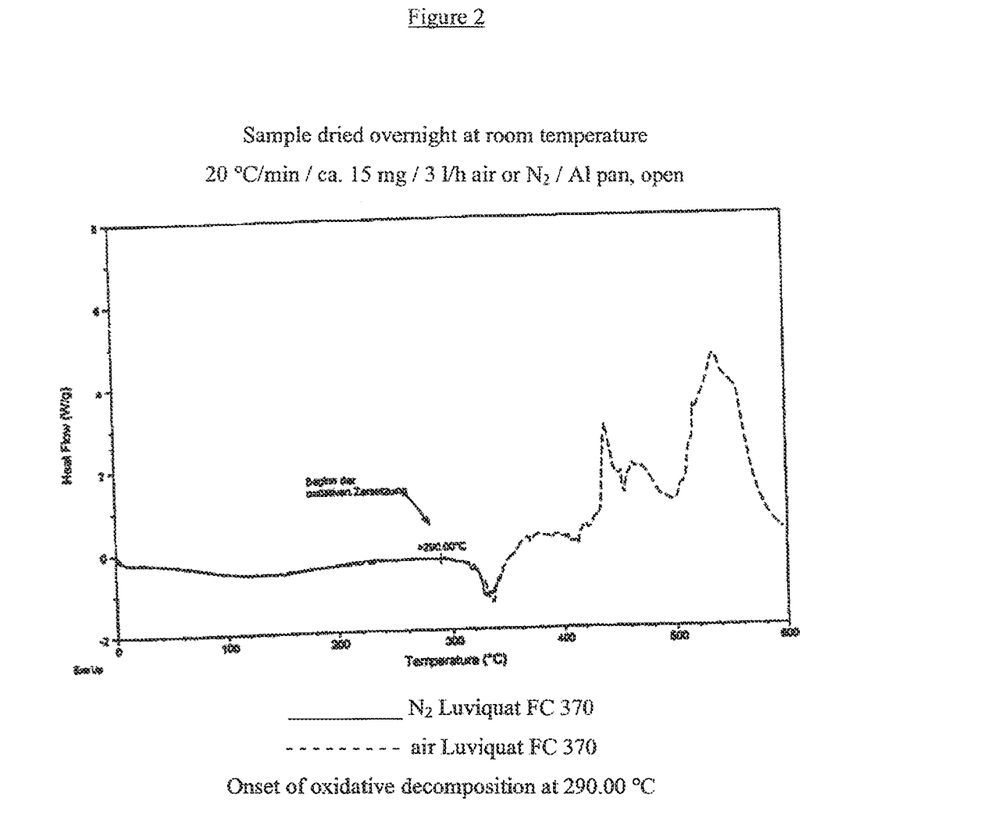
FIG. 2 is a graph showing DSC measurements under an air atmosphere and under nitrogen for Luviquat FC 370 film-forming polymer.
Figure 3:
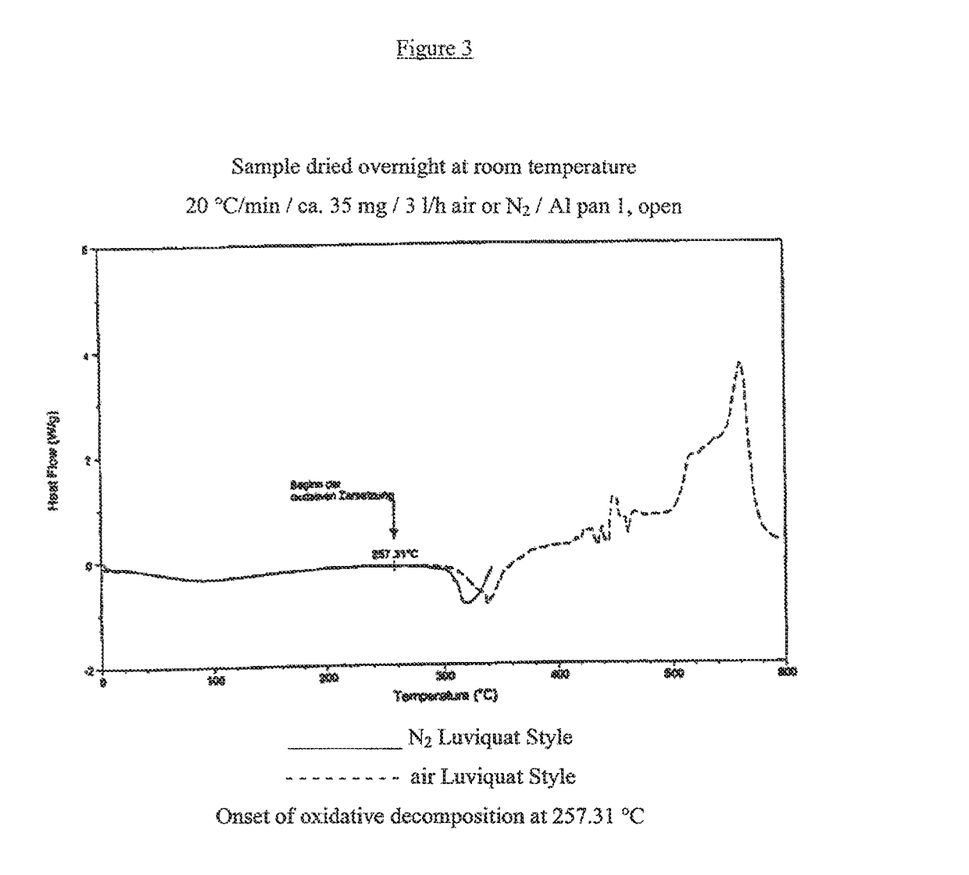
FIG. 3 is a graph showing DSC measurements under an air atmosphere and under nitrogen for Luviquat Style film-forming polymer.
Figure 4:
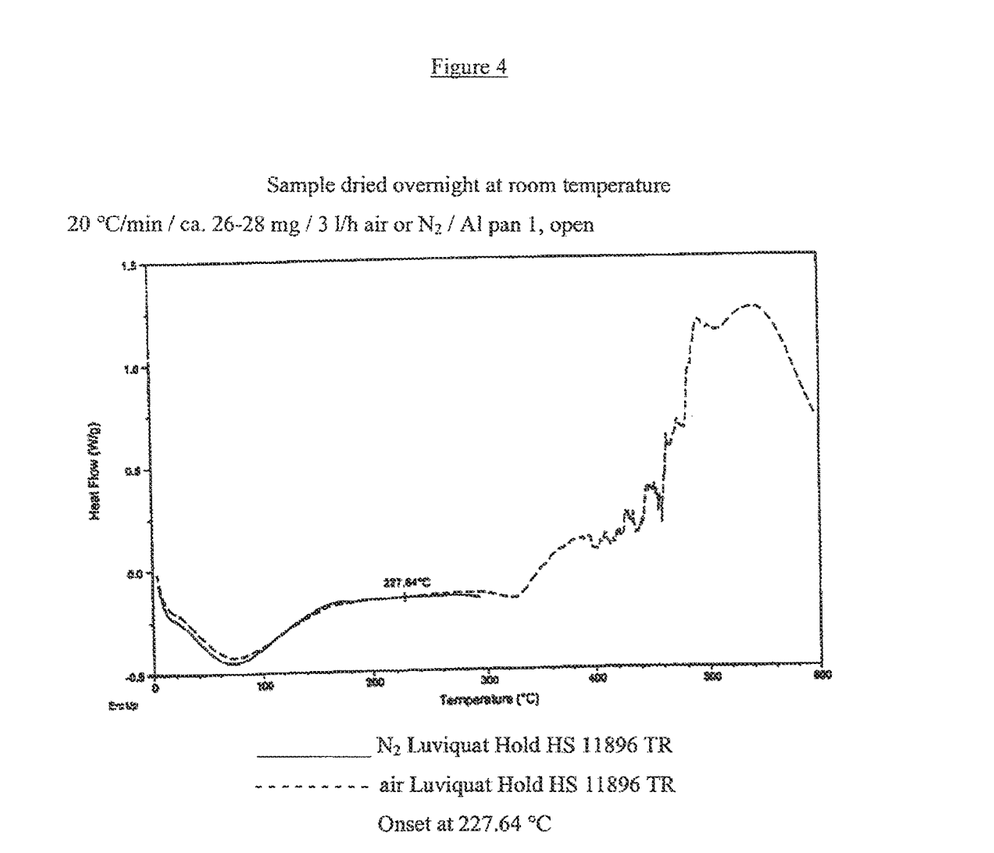
FIG. 4 is a graph showing DSC measurements under an air atmosphere and under nitrogen for Luviquat Hold film-forming polymer.
Figure 5:
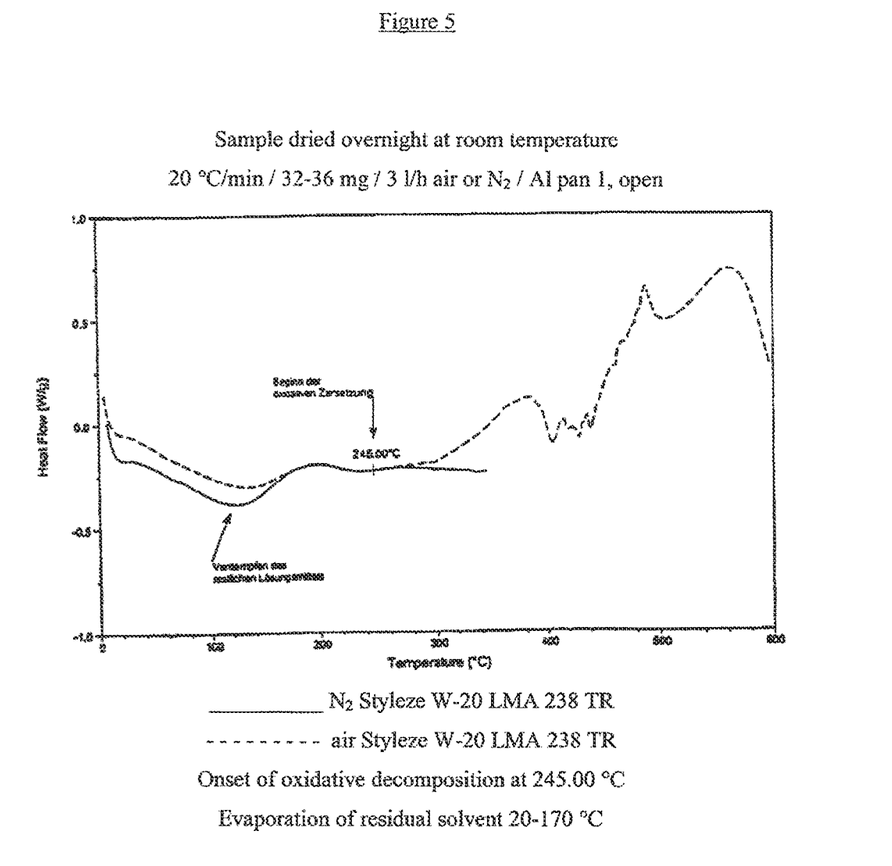
FIG. 5 is a graph showing DSC measurements under an air atmosphere and under nitrogen for Styleze W-20 film-forming polymer.
Figure 6:
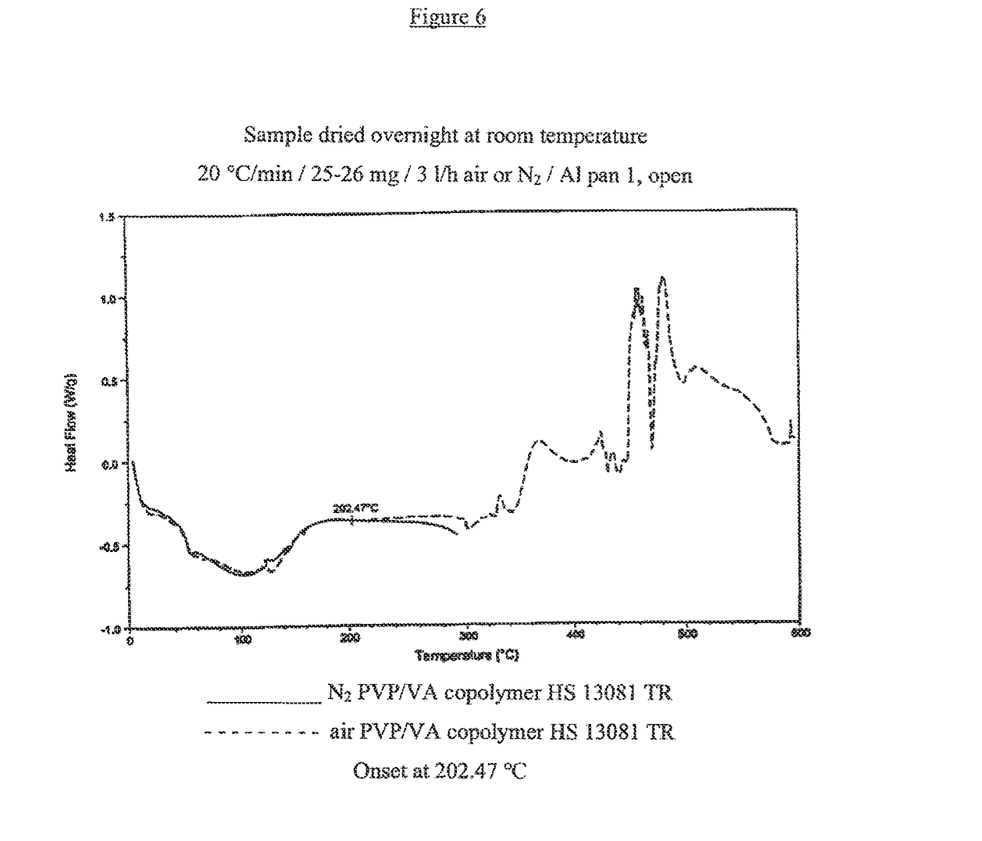
FIG. 6 is a graph showing DSC measurements under an air atmosphere and under nitrogen for PVP/VA-copolymer.
Figure 7:
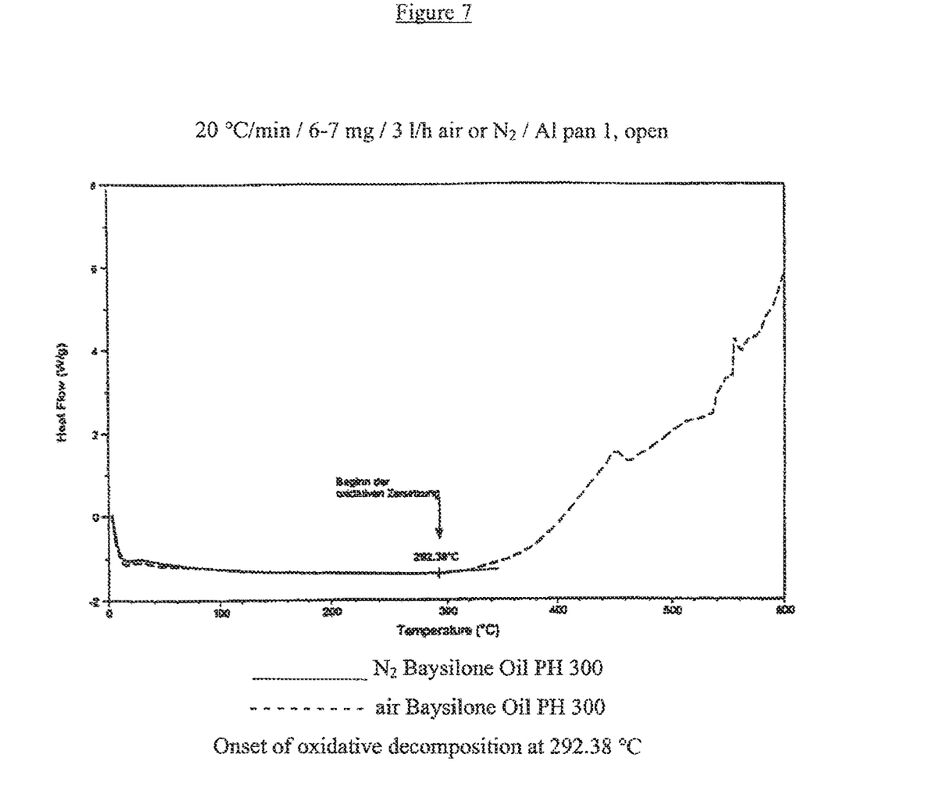
FIG. 7 is a graph showing DSC measurements under an air atmosphere and under nitrogen for Baysilone oil PH 300 silicone oil.
Figure 8:
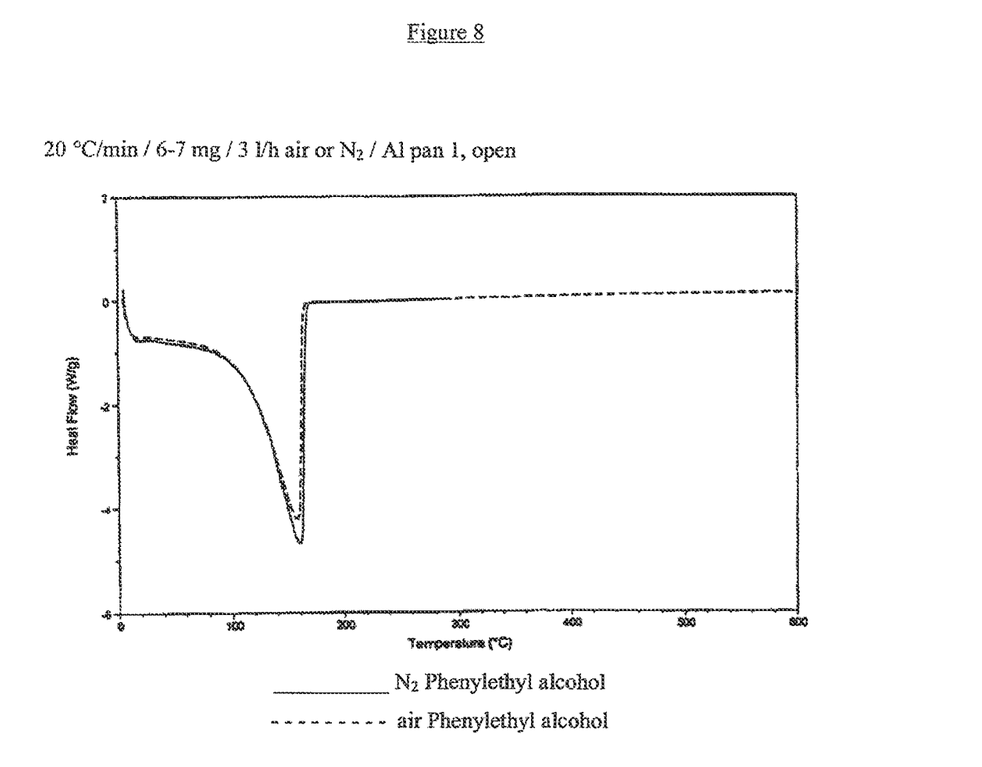
FIG. 8 is a graph showing DSC measurements under an air atmosphere and under nitrogen for phenylethyl alcohol.

The DSC measurements of preferred ingredients are given below solely as examples, such as the protein hydrolyzate Promois Silk (FIG. 1), the film-forming polymers Luviquat FC 370 (FIG. 2), Luviquat Style (FIG. 3), Luviquat Hold (FIG. 4), Styleze W-20 (FIG. 5), PVPNA-copolymer (FIG. 6), the silicone oil Baysilone oil PH 300 (FIG. 7) and the aroma phenylethyl alcohol (FIG. 8).

Whereas in FIGS. 1-7, the decomposition temperature determined from the DSC curves, measured by the exothermic deviations, both under an air atmosphere and under nitrogen, is above 200° C., there is no decomposition according to the DSC curves in FIG. 8 for the aroma phenylethyl alcohol. Phenylethyl alcohol evaporates without decomposition at about 170° C.

The inventive compositions preferably comprise both hair-care and hair-shaping active principles. According to the invention, these active principles must be stable to thermal decomposition up to 200° C.

The inventive hair treatment agents preferably comprise water and/or ethanol as the solvent.

The inventive compositions can comprise, for example, protein hydrolyzates and/or amino acids and their derivatives as hair-care components, in so far as they are stable up to 200° C. to thermal decomposition. Protein hydrolyzates are product mixtures obtained by acid-, base- or enzyme-catalyzed degradation of proteins (albumins). According to the invention, the term "protein hydrolyzates" is also understood to mean total hydrolyzates as well as individual amino acids and their derivatives as well as mixtures of different amino acids. According to the invention, the added protein hydrolyzates can be of both vegetable as well as animal or marine or synthetic origin.

Animal protein hydrolyzates are, for example, silk protein hydrolyzates, which can also be present in the form of their salts. They are marketed, for example under the trade name "Promois® (Interorgana)". An inventively preferred temperature-stable animal protein hydrolyzate is Promois Silk 1000.

Exemplary vegetable protein hydrolyzates are wheat protein hydrolyzates that are inventively preferred vegetable protein hydrolyzates.

The preparations used according to the invention preferably comprise the protein hydrolyzates or their derivatives in quantities of 0.1 to 10 wt. %, based on the total composition. Quantities of 0.1 to 5 wt. % are particularly preferred.

The inventive compositions can comprise temperature-stable cationic polymers.

Cationic polymers are understood to mean polymers that, in their main chain or side chain, have groups that can be "temporarily" or "permanently" cationic. "Permanently cationic" refers, according to the invention, to those polymers, which independently of the pH of the medium, have a cationic group. These are generally polymers, which comprise a quaternary nitrogen atom, in the form of an ammonium group, for example. Preferred cationic groups are quaternary ammonium groups. In particular, those polymers in which the quaternary ammonium groups are bonded through a $C_{1-4}$ hydrocarbon group to a polymer backbone of acrylic acid, methacrylic acid or their derivatives, have proved to be particularly suitable.

Homopolymers of the general formula (III), in which $R^{18}$=—H or —$CH_3$, $R^{19}$, $R^{20}$ and $R^{21}$ independently of each other are selected from $C_{1-4}$ alkyl, -alkenyl or -hydroxyalkyl groups, m=1, 2, 3 or 4, n=a natural number and $X^-$ is a physiologically compatible organic or inorganic anion, as well as copolymers, essentially consisting of the monomer units listed in formula (III) as well as non-ionic monomer units, are particularly preferred cationic polymers. Regarding these polymers, those that are preferred in accordance with the invention meet at least one of the following conditions:

$R^{18}$ stands for a methyl group $R^{19}$, $R^{20}$ and $R^{21}$ stand for methyl groups m has the value 2.

Exemplary physiologically compatible counter ions $X^-$ include halide ions, sulfate ions, phosphate ions, methosulfate ions as well as organic ions such as lactate, citrate, tartrate and acetate ions. Halide ions are preferred, particularly chloride.

A particularly suitable homopolymer is the optionally crosslinked poly(methacryloyloxyethyl trimethyl ammonium chloride) with the INCI name Polyquarternium-37. Crosslinking can be effected, when desired, with the help of olefinically polyunsaturated compounds, for example divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose. Methylene bisacrylamide is a preferred crosslinking agent.

The homopolymer is preferably employed in the form of a non-aqueous polymer dispersion that should have a polymer content of not less than 30 wt. %. Such polymer dispersions are commercially available under the names Salcare® SC 95 (ca. 50% polymer content, additional components: mineral oil (INCI name: Mineral Oil) and tridecyl-polyoxypropylene polyoxyethylene ether (INCI name: PPG-1-Tridecyth-6)) and Salcare® SC 96 (ca. 50% polymer content, additional components: mixture of diesters of propylene glycol with a mixture of caprylic- and capric acid (INCI name: Propylene Glycol Dicaprylate/Dicaprate) and tridecyl-polyoxypropylene polyoxyethylene ether (INCI name: PPG-1-Tridecyth-6)).

Copolymers with monomer units according to formula (III) preferably comprise acrylamide, methacrylamide, $C_{1-4}$ alkyl esters of acrylic acid and $C_{1-4}$ alkyl esters of methacrylic acid as the non-ionic monomer units. Acrylamide is particularly preferred among these monomers. These copolymers can also be crosslinked, as in the case of the above-described homopolymers. An inventively preferred copolymer is the crosslinked acrylamide/methacryloyloxyethyl trimethyl ammonium chloride copolymer. Such copolymers, in which the monomers are present in a weight ratio of about 20:80, are commercially available as a ca. 50% conc. non-aqueous polymer dispersion named Salcare® SC 92.

Further preferred cationic polymers are, for example quaternized cellulose derivatives, available under the names Celquat® and Polymer JR®. The compounds Celquat® H 100, Celquat® L 200 and Polymer JF®400 are preferred quaternized cellulose derivatives, cationic alkyl polyglycosides according to DE-PS 44 13 686, cationic honey, for example the commercial product Honeyquat® 50, cationic guar derivatives, such as in particular the products marketed under the trade names Cosmedia® Guar and Jaguar®, polysiloxanes with quaternary groups, such as, for example, the commercially available products Q2-7224 (manufacturer: Dow Corning; a stabilized trimethylsilylamodimethicone), Dow Corning® 929 emulsion (comprising a hydroxylamino-modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80), polymeric dimethyl diallyl ammonium salts and their copolymers with esters and amides of acrylic acid and methacrylic acid. The commercially available products Merquat®100 (poly(dimethyl diallyl ammonium chloride)) and Merquat®550 (dimethyl diallyl ammonium chloride-acrylamide copolymer) are examples of such cationic polymers.

copolymers of vinyl pyrrolidone with quaternized derivatives of dialkylamino acrylate and dialkylamino methacrylate, such as, for example vinyl pyrrolidone-dimethylaminoethyl methacrylate copolymers quaternized with diethyl sulfate. Such compounds are commercially available under the trade names Gafquat®734 and Gafquat®755.

vinyl pyrrolidone-vinylimidazolium methochloride copolymers, as are offered under the names Luviquat® FC 370, FC 550, FC 905, HM 552 and Hold.

quaternized polyvinyl alcohol and also the polymers known under the INCI designations
Polyquaternium 2,
Polyquaternium 17,
Polyquaternium 18 and
Polyquaternium 27 having quaternary nitrogen atoms in the polymer main chain.

Polymers designated as Polyquaternium-24 (commercial product e.g. Quatrisoft® LM 200) can also be employed as cationic polymers. The copolymers of vinyl pyrrolidone are also usable according to the invention, such as the commercially available products Copolymer 845 (manufacturer: ISP), Gaffix® VC 713 (manufacturer: ISP), Gafquat®ASCP 1011, Gafquat®HS 110, Luviquat®8155 and Luviquat® MS 370.

Further inventive cationic polymers are the "temporarily cationic" polymers. These polymers usually comprise an amino group that is present at specific pH values as the quaternary ammonium group and is thus cationic. Chitosan and its derivatives, such as for example the commercially available Hydagen® CMF, Hydagen® HCMF, Kytamer® PC and Chitolam® NB/101 are preferred. Chitosans are deacetylated chitins that are commercially available with various degrees of deactylation and various degrees of degradation (molecular weights). Their manufacture is described, for example in DE 44 40 625 A1 and in DE 1 95 03 465 A1.

Particularly well-suited chitosans have a deacetylation degree of at least 80% and a molecular weight of $5 \times 10^5$ to $5 \times 10^6$ (g/mol).

The chitosan has to be converted into the salt form for the manufacture of the inventive preparations. This can be effected by dissolution in dilute aqueous acids. Both mineral acids, such as e.g. hydrochloric acid, sulfuric acid and phosphoric acid and also organic acids, such as e.g. low molecular weight carboxylic acids, polycarboxylic acids and hydroxycarboxylic acids are suitable acids. Moreover, higher molecular weight alkyl sulfonic acids or alkyl sulfuric acids or organophosphoric acids can also be used, when they possess the required physiological compatibility. Suitable acids for converting chitosan into the salt form are e.g. acetic acid, glycolic acid, tartaric acid, malic acid, citric acid, lactic acid, 2-pyrollidinone-5-carboxylic acid, benzoic acid or salicylic acid. Low molecular weight hydroxycarboxylic acids are preferably used, such as e.g. glycolic acid or lactic acid.

Preferred cationic, film-forming polymers are the vinyl pyrrolidone/ethoimidazolinium chloride copolymers, offered under the name "Luviquat®", e.g. Luviquat FC 370 (INCI name: Polyquaternium-16), Luviquat Style (INCI name: Polyquaternium-16) und Luviquat Hold (INCI name: Polyquaternium-46), as well as the cationic terpolymer of vinyl pyrrolidone, dimethylaminopropyl methacrylamide and lauryl dimethyl propylmethacrylamido ammonium chloride, known according to INCI as Polyquaternium-46 that is commercially available as Styleze W.

The inventive compositions preferably comprise cationic polymers in amounts of 0.2-4 wt. %, preferably 0.5-2 wt. %.

Moreover, the inventive compositions can also comprise temperature-stable non-ionic polymers.

Suitable nonionogenic polymers are, for example:

vinyl pyrrolidone-vinyl ester copolymers, such as, for example, those marketed by BASF under the trade name Luviskol®, Luviskol® VA 64 and Luviskol® VA 73, each vinyl pyrrolidone-vinyl acetate copolymers, are preferred non-ionic polymers.

cellulose ethers, such as hydroxypropyl cellulose, hydroxyethyl cellulose, and methyl hydroxypropyl cellulose, as marketed for example under the trademarks Culminal® and Benecel® (AQUALON).

shellac.

polyvinyl pyrrolidones, as are marketed, for example, under the designation Luviskol® (BASF).

siloxanes. These siloxanes can be both water-soluble and water-insoluble. Both volatile and non-volatile siloxanes are suitable, whereby non-volatile siloxanes are understood to mean such compounds with a boiling point above 200° C. at normal pressure. Preferred siloxanes are polydialkylsiloxanes, such as, for example polydimethylsiloxane, polyalkylarylsiloxanes, such as, for example polyphenylmethylsiloxane, ethoxylated polydialkylsiloxanes as well as polydialkylsiloxanes, which comprise amine and/or hydroxyl groups.

glycosidically substituted silicones according to EP 0 612 759 B1.

The water-soluble, film-forming vinyl pyrrolidone/vinyl acetate copolymer, for example, is preferred according to the invention and is commercially available under the trade name PVPNA W-635 (INCI name: VP/VA Copolymer).

The inventive preparations preferably comprise the non-ionic polymers in amounts of 0.5-10 wt. %, particularly preferably in amounts of 1-5 wt. %.

In addition, the inventive compositions can comprise temperature-stable surfactants.

The term "surfactant" is understood to mean surface-active substances that form adsorption layers at surfaces and interfaces or can aggregate in volume phases to micelle colloids or lyotropic mesophases. One distinguishes between anionic surfactants that consist of a hydrophobic group and a negatively charged hydrophilic head group, amphoteric surfactants that carry both a negative and a compensating positive charge, cationic surfactants that besides a hydrophobic group have a positively charged hydrophilic group, and non-ionic surfactants that have no charges but rather strong dipole moments and are strongly hydrated in aqueous solution. More detailed definitions and properties of surfactants can be found in "H.-D. Dörfler, Grenzflächen-und Kolloidchemie, VCH Verlagsgesellschaft mbH. Weinheim, 1994". The definitions given above can be found as of page 190 in this publication.

Temperature-stable cationic surfactants of the types quaternary ammonium compounds, the esterquats and the amidoamines are particularly preferred. Preferred quaternary ammonium compounds are ammonium halides, particularly chlorides and bromides, such as alkyl trimethyl ammonium chlorides, dialkyl dimethyl ammonium chlorides and trialkyl methyl ammonium chloride, e.g. cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride, as well as the imidazolium compounds known under the INCI designations Quaternium-27 and Quaternium-83. The long alkyl chains of the abovementioned surfactants have preferably 10 to 18 carbon atoms.

Esterquats are known compounds, which both comprise at least one ester function and also a quaternary ammonium group as structural elements. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are marketed, for example, under the trade names Stepantex®, Dehyquart® and Armocare®. The products Armocare® VGH-70, an N,N-bis (2-palmitoyloxyethyl) dimethyl ammonium chloride, as well as Dehyquart® F-75, Dehyquart®C-4046, Dehyquart® L80 and Dehyquart® AU 35 are examples of such esterquats.

The alkylamidoamines are normally manufactured by the amidation of natural or synthetic fatty acids and fatty acid fractions with dialkylaminoamines. According to the invention, a particularly suitable compound from this substance group is represented by stearamidopropyldimethylamine, commercially available under the designation Tegamid® S 18.

According to the invention, cetyl trimethyl ammonium chloride is preferably used and is available under the name Genamin CTAC.

The inventive compositions preferably comprise the cationic surfactants in amounts of 0.1-1 wt. %, particularly preferably 0.2-0.6 wt. %.

Moreover, the inventive compositions can comprise suitable silicone oils as the conditioning agents, such as e.g. Baysilone Oil PH 300.

The inventive preparations preferably comprise the silicone oils in amounts of 0.1-1 wt. %, particularly preferably in amounts of 0.1-0.5 wt. %.

The inventive compositions do not comprise perfume oils that often have a partially unknown composition and a decomposition temperature of below 200° C. as the fragrance, but rather certain toxicologically harmless aromas that evaporate without decomposition. According to the invention, preferred aromas are 2-phenylethanol, which imparts a rose odor and evaporates at ca. 160° C., and 2-phenylethyl acetate, which has a boiling point of 232.6° C. at 101.3 kPa.

With regard to further standard ingredients, reference is expressly made to monographs known to the person skilled in the art, for example K. Schrader, Grundlagen und Rezepturen der Kosmetika, Dr. Alfred Hüthig Verlag, Heidelberg.

The inventive hair treatment agents can be formulated into the customary application forms, such as e.g. spray solutions, aerosol sprays, foam or shakeable lotions. According to the invention, the preferred formulation is the spray solution.

The following embodiments clarify the invention without limiting it in any way.

EXAMPLE 1

Spray Solution

| | |
|---|---|
| demineralized water | 73.38 wt. % |
| cationized wheat protein hydrolyzate | 0.6 wt. % |
| Promois Silk 1000[1] | 0.5 wt. % |
| denatured ethanol 96 vol. % | 20.0 wt. % |
| ortho-phosphoric acid | 0.02 wt. % |
| Genamin CTAC[2] | 0.5 wt. % |
| PVP/VA W-635[3] | 5.0 wt. % |

[1] Silk protein hydrolyzate; INCI name: Hydrolyzed Silk
[2] Trimethyl hexadecyl ammonium chloride (ca. 29 wt. % active substance in water); INCI name: Cetrimonium Chloride
[3] Vinyl pyrrolidone-vinyl acetate copolymer, stabilized with 0.05 wt. % dodecyl trimethyl ammonium chloride; INCI name: VP/VA Copolymer

EXAMPLE 2

Spray Solution

| | |
|---|---|
| demineralized water | 68.47 wt. % |
| Promois Silk 1000) | 1.0 wt. % |
| Pearlpurin PP[4)] | 0.01 wt. % |
| denatured ethanol 96 vol. % | 20.0 wt. % |
| ortho-phosphoric acid | 0.02 wt. % |
| Genamin CTAC | 0.5 wt. % |
| PVP/VA W-635 | 10.0 wt. % |

[4)]Mixture of a starch hydrolyzate and ground freshwater pearls; INCI name: Maltodextrin and Pearl Powder

The invention claimed is:

1. A method for styling hair, comprising the steps of:
   a. providing a composition consisting of
   vinyl pyrrolidone/vinyl acetate copolymer;
   a solvent chosen from water, ethanol, or a combination thereof;
   a silk protein hydrolyzate;
   ortho-phosphoric acid;
   cetrimonium chloride;
   at least one ingredient chosen from i) a mixture of starch hydrolyzate and pearl powder or ii) cationized wheat protein hydrolyzates, and
   b. applying the composition to hair; and
   c. thermally treating the composition-treated hair.

2. The method of claim 1, wherein the step of thermally treating the hair is by using a hot iron, curling rod, or hair dryer with diffuser.

3. The method of claim 2, wherein the thermal treatment step comprises the step of curling or crimping.

4. The method of claim 2, wherein the thermal treatment step comprises the step of smoothing the hair.

5. The method of claim 1, wherein the step of applying includes the step of spraying the composition to hair.

* * * * *